United States Patent [19]

Herget et al.

[11] Patent Number: 6,139,962
[45] Date of Patent: Oct. 31, 2000

[54] SURFACE-MODIFIED PLATELET-SHAPED SUBSTRATES

[75] Inventors: Gerhard Herget, Ober-Ramstadt; Brigitte Husseini, Darmstadt, both of Germany

[73] Assignee: Merck Patent Gesellschaft mit beschrankter Haftung, Germany

[21] Appl. No.: 09/161,291

[22] Filed: Sep. 28, 1998

[30] Foreign Application Priority Data

Sep. 26, 1997 [DE] Germany .............................. 197 42 551
Jan. 20, 1998 [DE] Germany .............................. 198 01 809

[51] Int. Cl.$^7$ .............................. B32B 9/00; C04B 14/00; B05D 7/00
[52] U.S. Cl. .......................... 428/404; 106/400; 106/415; 427/215; 427/219
[58] Field of Search ...................................... 106/400, 401, 106/415, 417, 481, 482; 428/357, 363, 364, 368, 402, 403, 404; 427/215, 216, 219

[56] References Cited

U.S. PATENT DOCUMENTS 5,352,287  10/1994  Wason et al. ........................... 106/416

*Primary Examiner*—Paul Thibodaau
*Assistant Examiner*—Sheeba Ahmed
*Attorney, Agent, or Firm*—Millen, White, Zelano & Branigan, P.C.

[57] ABSTRACT

The present invention relates to surface-modified pigments based on platelet-shaped substrates, having improved settling and reagitation characteristics, and to their preparation processes and use.

14 Claims, No Drawings

SURFACE-MODIFIED PLATELET-SHAPED SUBSTRATES

BACKGROUND OF THE INVENTION

The present invention relates to surface-modified pigments based on platelet-shaped substrates having improved settling and reagitation characteristics, and to their preparation processes and use.

Coating compositions, such as lacquers, paints, printing inks, etc., comprising pigments based on platelet-shaped substrates are subject to handling problems insofar as the pigments, owing to their size and density, settle readily and may then become compacted to form a highly solid sediment cake. This cake can generally be reagitated only with very great difficulty. This situation affects in particular the storage of lacquers, paints and printing inks and their processing. Furthermore, it is common when pigmenting plastics, basecoat systems, etc. to observe agglomeration of the pigments. Homogeneous distribution of the pigment in their respective matrix is difficult if not impossible to achieve.

Thus numerous methods have been developed, inter alia, in order to solve the problem of the incorporation and handling of platelet-shaped pigments in coating compositions.

DE 3627329 and the EP's 0306056 and 0268918 disclose that modified platelet-shaped substrates with a polymer coating and, respectively, following treatment with coupling reagents such as organotitanates, or organosilanes in covering compositions exhibit improved settling and reagitation characteristics.

Reagitation can also be facilitated by treating the coating compositions with additives, which bring about targeted flocculation (house of cards effect), pseudoplastic and/or thixotropic behavior, steric repulsion and/or electrostatic repulsion of the pigments.

Additives with thixotropic characteristics are described in EP 0198519 and DE-A 1805693. DE 3922128 discloses that mixing a suspension of a platelet-shaped substrate with spherical particles such as $SiO_2$, $TiO_2$ and $ZrO_2$, for example, produces deagglomerated and readily dispersible pigments.

In EP 0523357, pearl luster pigments are treated with diurea derivatives, while EP 0515928 discloses the surface modification of pigments with polyacrylates. EP 0650144 discloses the coating of pearl luster pigments with $SiO_2$/$Al_2O_3$ and $SiO_2$/$ZrO_2$.

All of these additives may, however, have an adverse effect on the quality of the coating. In particular, the brilliance and color properties, in the case of pearl luster pigments, and the uniformity of the coating may be impaired. These impairments are generally greater the higher the concentration of additives employed.

SUMMARY OF THE INVENTION

An object was therefore to find surface-modified pigments based on platelet-shaped substrates which when incorporated into a coating composition exhibit to a lesser extent if at all the disadvantages observed in the case of coating compositions with conventional pigmentation.

It has now surprisingly been found that pigments which are based on platelet-shaped substrates and are coated with a phyllosilicate from the group, preferably, of the smectites, e.g., having a diameter of 0.1–25 nm [particle size in the activated (fully dispersed) state] exhibit improved settling and reagitation characteristics in coating compositions.

The invention therefore provides surface-modified pigments which are based on a platelet-shaped substrate and which, in order to improve the settling and reagitation characteristics, are coated with a phyllosilicate having a diameter of 0.1–25 nm.

The invention also provides a process for preparing surface-modified platelet-shaped substrates, characterized in that platelet-shaped substrates are mixed in dry form with a phyllosilicate, preferably from the group of the smectites, in a mixing vessel.

The simple mixture of pearl luster pigment with phyllosilicate exhibits, more or less unacceptably, agglomerations and severe loss of gloss. It has surprisingly now been found that if the active substance is pretreated (dispersed and spray-dried) it is possible to produce a powder which shows little propensity to agglomerate and no loss of gloss.

Also surprising is the observation that there is no lasting effect on the optical properties of the coated substrates. The concentration in which the natural or synthetic silicate is employed can be 0.2–30% by weight, based on the pigment, but is preferably 0.5–20% by weight, in particular 0.2–5% by weight. The pigments of the invention are also notable for good compatibility with the other components of coating systems and for their good processability, high level of freedom from dust, and stability. In connection with the ease of incorporation of pigments into formulations, a delayed settling behavior and an improved reagitation behavior of any sediment are observed. On the basis of their very good feel on the skin, the pigments of the invention are also highly suitable for cosmetic formulations.

All known platelet-shaped metals, metal oxides, mica pigments and other platelet-shaped substrates can be covered in accordance with the process of the invention.

Examples thereof are natural and synthetic mica, talc, kaolin, $SiO_2$ flakes, $TiO_2$ flakes, aluminium flakes, or other comparable minerals, platelet-shaped alumina or iron oxide, LCPs, holographic pigments and bismuth oxychloride.

Since the process does not necessitate any high shear forces, it is also outstandingly suited to the coating of pearl luster pigments.

It is possible to use all customary pearl luster pigments, examples being micas coated with colored and colorless metal oxides, such as $TiO_2$, $Fe_2O_3$, $SnO_2$, $Cr_2O_3$, $ZnO$ and other metal oxides, alone or in a mixture, in a uniform layer or in successive layers. These pigments are known, for example, from the German Patents and Patent Applications 1467468, 1959998, 2009566, 2214545, 2215191, 2244298, 2313331, 2522572, 3137808, 3137809, 3151343, 3151354, 3151355, 3211602 and 3235017 are obtainable commercially, for example under the brand name Iriodin® from Merck KGaA, Darmstadt, Germany. It is also possible to modify conductive pigments as are known, for example, from EP 0373575 and are sold in commerce under the brand name Minatec® by Merck KGaA, Darmstadt, Germany.

Suitable phyllosilicates are, in particular, those from the group of the smectite series, such as the montmorillonite/beidellite series. These smectites are noted in particular for their pronounced swelling behavior. These products are sold in commerce, for example, under the brand name Laponite, a synthetic sodium-magnesium-lithium silicate similar to hectorite, by Laporte UK or by Südchemie, FRG under the name Optigel CG, a bentonite, or Tixogel PE, an organophilic hydrophobized smectite. Also suitable are all micaceous silicates of the vermiculite series and the illite series, and the micas themselves (muscovite, phlogopite, biotite). Highly preferred is the platelet-shaped nature of the particles and their ability to be digested in the spray-drying process.

For the surface modification it is also possible to employ mixtures of the abovementioned phyllosilicates and also modified phyllosilicates.

The phyllosilicates are preferably employed in an activated form; in other words, the silicates are dispersed in water, converted into a sol and then spray-dried.

The use of an activated phyllosilicate makes the surface modification of pigments easier insofar as there is no need for the pigment to be pasted up nor for any solvent.

When forming the sol, it is also possible to add customary additives to the aqueous dispersion, examples being dispersing auxiliaries, such as polyphosphates, for example, especially sodium pyrophosphate or sodium hexametaphosphate. The overall concentration of all additives, however, based on the phyllosilicate, should not exceed 10% by weight. Preferably, the content of additives should lie between 0.1 and 5% by weight, in particular 0.5–2% by weight.

The process of the invention is therefore simple and easy to operate. The composition is prepared by dry-mixing the abovementioned active substances with the pigments in, for example, a tumble mixer, flywheel mixer, bucket mixer or fluid mixer, with preference being given to low-speed mixers owing to the relatively high fragility of the substrates. Since no high shear forces are necessary in the course of pigment preparation, the process of the invention is also outstandingly suitable for pearl luster pigments.

If desired, a humectant may be added to the mixture of pigment and modifier.

The pigments of the invention can likewise be employed for preparing pigment preparations. For this purpose the pigments are pasted up with 0.5–30% by weight of water or an organic solvent or solvent mixture. Pigment preparations of this kind comprise at least 80% by weight of the pigments of the invention. In addition, the aqueous or solvent-containing mixture may include up to 30% by weight of binder or resin. The resins are preferably selected from the series of the resins employed in the printing sector. The pigment content of these mixture is then at least 40% by weight. The pigment preparation may comprise additional components, examples being defoamers, wetting agents, anti-settling agents, flow control agents, siccatives and thixotropic agents. In addition, the pigment preparation can be extruded, granulated or pelletized and then, if desired, dried by means, for example, of spray drying or fluidized-bed drying, etc. In the dried state the pigment content is at least 70% by weight. The pigment preparations and dry preparations prepared therefrom can be incorporated into all known utility media, especially into lacquers, paints and printing inks. In addition, granules can be produced from resin melts under the action of temperature.

The invention likewise provides pigment preparations comprising the pigments of the invention.

The pigments of the invention are compatible with a large number of color systems, preferably from the sector of lacquers, paints and printing inks.

The invention therefore also provides for the use of the surface-modified pigments in formulations such as paints, printing inks, lacquers and plastics and for cosmetics preparation.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German applications No. 19742551.8, filed Sep. 26, 1997, and 19801809.6, filed Jan. 20, 1998 are hereby incorporated by reference.

EXAMPLES

Example 1

200 g of Laponite RDS (product of Laporte, UK) are added with stirring at 500 rpm to 1800 g of deionized water at 40° C., and stirring is continued at 700 rpm for 1 hour. The result is a sol having a viscosity of 12 s 4 mm DIN cup. The sol is dried in a Niro Atomizer Minor spray drier having a theoretical throughput of 5–7 l/h at 95–100° C. and 4 bar.

Example 2

100 g of Laponite RD (Laporte, UK) are added to 1900 g of a 10% strength sodium pyrophosphate solution, which is heated at 40° C., with stirring using a Dispermat AE from Getzmann with a toothed disc of diameter 6 cm, and the mixture is homogenized at 2000 rpm for 2×5 minutes. The mixture is subsequently transferred with 900 g of deionized water into a 3 l cylindrical glass vessel and is stirred again at 800 rpm for 10 minutes. The sol is dried in a Niro Atomizer Minor spray drier at 95–110° C. and 4 bar.

Example 3

1000 g of Optigel CG (Südchemie, FRG) are added to 1900 g of a 10% strength sodium pyrophosphate solution, which is heated at 40° C., with stirring using a Dispermat AE from Getzmann with a toothed disc of diameter 6 cm, and the mixture is homogenized at 2000 rpm for 2×5 minutes. The mixture is subsequently transferred with 900 g of deionized water into a 3 l cylindrical glass vessel and is stirred again at 800 rpm for 10 minutes. The sol is dried in a Niro Atomizer Minor spray drier at 95–110° C. and 4 bar.

Example 4

250 g of Iriodin® 123 Hellglanzsatin [bright gloss satin] ($TiO_2$/mica pigment of particle size 5–40 µm from Merck KGaA, FRG) are mixed in dry form with 3.8 g of spray-dried Laponite RDS from Experiment 1. The mixing time is 15 minutes. The result is a homogeneous material which is employed in this form for the subsequent experiments.

Example 5

The pigment from Experiment 4 is compared with the starting material Iriodin® 123 in a coating card (pigment concentration 1.7% by weight, nitrocellulose/polyacrylate binder). There are no visible differences.

Measurement of the Lab values on a Hunterlab spectrogoniometer shows no deviations from the measurement tolerance.

Example 6

39 g of pigment from Experiment 4 are incorporated into 91 g of a binder, Synthacryl SW175 (40% strength solution of acrylic resin in 2:1 $H_2O$/isopropanol) from Hoechst, and are adjusted with isopropanol to a flow time of 21±1 seconds. The pigment content is 22.3% by weight.

Example 7

39 g of Iriodin® 123 Hellglanzsatin are incorporated into 91 g of a binder, Synthacryl SW175 from Hoechst, and are adjusted with isopropanol to a flow time of 21±1 seconds. The pigment content is 24.2% by weight.

Example 8

50 ml of each of the colorants from Examples 6 and 7 are investigated for their settling behaviour in measuring cylinders over 30 days. After 30 days, the sediment of the modified pigment is 30 ml and is very easy to reagitate, while the sediment of the reference is 20 ml and is only moderately reagitatable. A mandrel passes right through the sediment of the modified pigment, whereas the reference shows a penetration depth of up to only 65%.

Example 9

39 g of pigment from Experiment 4 are incorporated into 91 g of a binder, GS 95 MB011TW (based on nitrocellulose) from Gebrüder Schmidt, Frankfurt, FRG, and are adjusted with 1-ethoxy-2-propanol to a flow time of 21 seconds 4 mm DIN cup. The pigment concentration is 21.6% by weight.

Example 10

39 g of Iriodin® 123 are incorporated into 91 g of a binder, GS 95 MB011TW from Gebrüder Schmidt, Frankfurt, FRG, and are adjusted with 1-ethoxy-2-propanol to a flow time of 21 seconds 4 mm DIN cup. The pigment concentration is 23.6% by weight.

Example 11

50 ml of each of the colorants from Experiments 9 and 10 are investigated for their settling behavior in measuring cylinders over 30 days. After 30 days, all of the sediments are 25 ml. Reagitation is generally difficult, although the modified pigment is perceptively easier to reagitate than the reference.

Example 12

3.8 g of spray-dried Laponite RDS from Experiment 1, and a solution of 60 g of polyethylene glycol 2000 (Merck) in 60 g of water, are added to 250 g of Iriodin® 123 Hellglanzsatin, and a homogenous mixture is formed. The moistened preparation is subsequently granulated in a laboratory granulator (Eirich) to a target particle size of 1–2 mm. The moist granules are dried in a fluidized bed and the resulting material is fractionated over 1.4 mm and 10 μm sieves. The target-size particles obtained are free flowing, free from dust and easy to meter.

Example 13

3.8 g of spray-dried Laponite RDS from Experiment 1, and a solution of 60 g of Laropal A 81 (BASF) in 60 g of ethanol, are added to 250 g of Iriodin® 123 Hellglanzsatin, and a homogenous mixture is formed. The moistened preparation is subsequently granulated in a laboratory granulator (Eirich) to a target particle size of 1–2 mm. The moist granules are dried in a fluidized bed and the resulting material is fractionated over 1.4 mm and 100 μm sieves. The target-size particles obtained are free flowing, free from dust and easy to meter.

Example 14

3.8 g of spray-dried Laponite RDS from Experiment 1, and a solution of 60 g of Cyracure Resin UVR 6110, are added to 250 g of Iriodin® 123 Hellglanzsatin, and a homogeneous mixture is formed. The preparation is subsequently granulated in a laboratory granulator (Eirich) to a target particle size of 1–2 mm. The target-size particles obtained are free flowing, free from dust and easy to meter.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A surface-modified pigment comprising a platelet-shaped substrate coated with an activated phyllosilicate.

2. A surface-modified pigment according to claim 1, wherein the phyllosilicate has a diameter of 0.1–25 nm.

3. A surface-modified pigment according to claim 1, wherein the content of phyllosilicate based on the overall pigment is 0.2–30% by weight.

4. A surface-modified pigment according to claim 1, wherein the phyllosilicate is a smectite.

5. A process for preparing a surface-modified platelet-shaped pigment according to claim 1, comprising dry-mixing a platelet-shaped substrate and phyllosilicate in a mixing vessel for subsequent activation.

6. A process according to claim 5, wherein the phyllosilicate activated by spray-drying a sol of the silicate optionally contains additives.

7. A process according to claim 6, wherein a dispersant is added to the sol prior to spray-drying.

8. A paint, lacquer, printing ink, plastic or cosmetic preparation comprising a surface-modified pigment according to claim 1.

9. A pigment preparation comprising at least 80% of a pigment according to claim 1 and 0.5–30% by weight of water or an organic solvent or solvent mixture.

10. A pigment preparation, comprising at least 70% by weight of a pigment according to claim 1 and up to 30% by weight of binder and/or resin.

11. A dry preparation comprising an extruded, pelletized or granulated preparation according to claim 9.

12. A paint, lacquer, printing ink, or plastic, comprising a pigment preparation according to claim 9.

13. A dry preparation comprising an extruded, pelletized or granulated and optionally dried preparation according to claim 10.

14. A paint, lacquer, printing ink, or plastic, comprising a pigment preparation according to claim 10.

\* \* \* \* \*